United States Patent [19]

Seidel

[11] Patent Number: 5,091,581
[45] Date of Patent: Feb. 25, 1992

[54] PROCESS FOR THE SELECTIVE PREPARATION OF N-SUBSTITUTED 1,4-DIAMINO-2-NITROBENZENES

[75] Inventor: Winfried Seidel, Fuchsrute, Fed. Rep. of Germany

[73] Assignee: Hans Schwarzkopf GmbH, Hamburg, Fed. Rep. of Germany

[21] Appl. No.: 518,710

[22] Filed: May 7, 1990

[30] Foreign Application Priority Data

May 26, 1989 [DE] Fed. Rep. of Germany ....... 3917113

[51] Int. Cl.$^5$ .................. C07C 209/14; C07C 269/04
[52] U.S. Cl. ..................... 564/412; 564/441; 560/22; 560/23; 560/24; 560/29; 560/30
[58] Field of Search ............ 560/22, 23, 24, 29, 560/30; 564/412, 414, 441

[56] References Cited

U.S. PATENT DOCUMENTS

| | | | |
|---|---|---|---|
| 4,005,217 | 1/1977 | Berg et al. | 424/300 |
| 4,125,601 | 11/1978 | Bugaut et al. | 560/22 |
| 4,470,826 | 9/1984 | Bugaut et al. et al. | 564/441 |
| 4,575,378 | 3/1986 | Seidel et al. | 564/441 |

FOREIGN PATENT DOCUMENTS 3141019 6/1991 Fed. Rep. of Germany ...... 564/441

OTHER PUBLICATIONS

R. Adams et al., (I), *J. Am. Chem. Soc.*, "Beta-Arylamino Ethanols", 45, pp. 785-790 (1923).
R. Adams et al. (II), *J. Am. Chem. Soc.*, "Tetrahydro-1,2,3-Oxazones and Substituted Gamma-Amino Propanols", 45, pp. 790-795 (1923).

*Primary Examiner*—Glennon H. Hollrah
*Assistant Examiner*—Mark W. Russell
*Attorney, Agent, or Firm*—Beveridge, DeGrandi & Weilacher

[57] ABSTRACT

The invention relates to a process for the selective preparation of $N^4$-substituted 1,4-diamino-2-nitrobenzenes of the general formula I

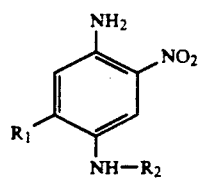

in which $R_1$ denotes hydrogen, halogen, ($C_1$-$C_4$) alkyl or ($C_1$-$C_4$) alkoxy, it being possible for the carbon atoms to be arranged in straight-chain or branched form, and $R_2$ represents a radical —COO—CH(A)—CH(B)—D with the meanings A=H, B=H, D=Cl, A=H, B=CH$_3$, D=Cl, A=H, B=H, D=CH$_2$Cl or A=CH$_3$, B=H and D=Cl (compounds of the general formula Ia) or a radical —CH(X)—CH(Y)—Z with the meanings X=H, Y=H, Z=OH, X=CH$_3$, Y=H, Z=OH, X=H, Y=H, Z=CH$_2$OH or X=H, Y=CH$_3$ and Z=OH (compounds of the general formula Ib)

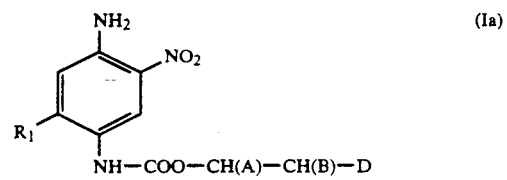

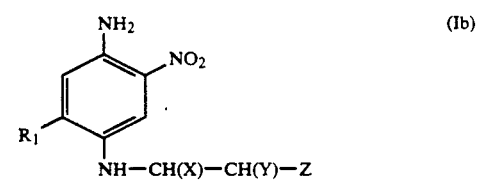

which is characterized in that 1,4-diamino-2-nitrobenzenes of the general formula II

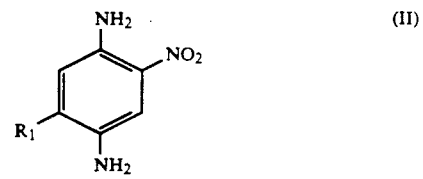

wherein $R_1$ has the abovementioned meaning, are reacted in a first stage with an approximately equimolar amount of a chloroalkyl chloroformate of the general formula Cl—COO—CH(A)—CH(B)—D, wherein A, B and D have the above-mentioned meanings, in a predominantly aqueous medium which contains—based on the water present—not more than 20 percent by weight of an organic solvent, and preferably in a purely aqueous medium to give carbamates of the general formula Ia and if appropriate these carbamates are converted into compounds of the general formula Ib in a second stage by means of treatment with a base.

6 Claims, No Drawings

PROCESS FOR THE SELECTIVE PREPARATION OF N-SUBSTITUTED 1,4-DIAMINO-2-NITROBENZENES

The invention relates to a process for the selective preparation of $N^4$-substituted 1,4-diamino-2-nitrobenzenes of the general formula I

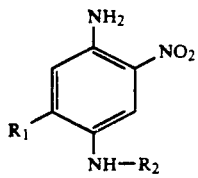

in which $R_1$ denotes hydrogen, halogen, ($C_1$-$C_4$) alkyl or ($C_1$-$C_4$) alkoxy, it being possible for the carbon atoms to be arranged in straight-chain or branched form, and $R_2$ represents a radical —COO—CH(A)—CH(B)—D with the meanings A=H, B=H, D=Cl, A=H, B=CH$_3$, D=Cl, A=H, B=H, D=CH$_2$Cl or A=CH$_3$, B=H and D=Cl (compounds of the general formula Ia) or a radical —CH(X)—CH(Y)—Z with the meanings X=H, Y=H, Z=OH, X=CH$_3$, Y=H, Z=OH, X=H, Y=H, Z=CH$_2$OH or X=H, Y=CH$_3$ and Z=OH (compounds of the general formula Ib)

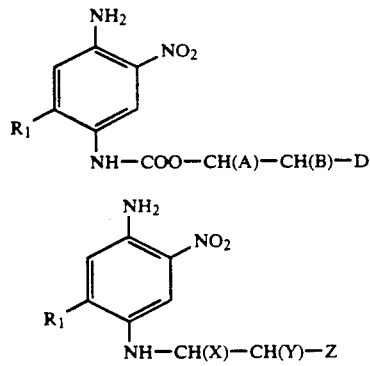

which is characterized in that 1,4-diamino-2-nitrobenzenes of the general formula II

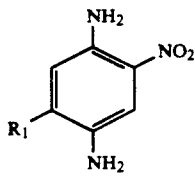

wherein $R_1$ has the abovementioned meaning, are reacted in a first stage with an approximately equimolar amount of a chloroalkyl chloroformate of the general formula Cl—COO—CH(A)—CH(B)—D, wherein A, B and D have the above-mentioned meanings, in a predominantly aqueous medium which contains—based on the water present—not more than 20 per cent by weight of an organic solvent, and preferably in a purely aqueous medium to give carbamates of the general formula Ia and if appropriate these carbamates are converted into compounds of the general formula Ib in a second stage by means of treatment with a base.

The invention furthermore relates to new $N^4$-substituted 1,4-diamino-2-nitrobenzenes of the general formula Ia, wherein $R_2$ represents a radical —COO—CH(A)—CH(B)—D and $R_1$, A, B and D have the abovementioned meaning, and their use for the preparation of compounds of the general formula Ib, wherein $R_2$ represents a radical —CH(X)—CH(Y)—Z and $R_1$, X, Y and Z have the abovementioned meaning, but excluding the compound $N^4$-($\beta$-chloroethoxycarbonyl)-5-methyl-1,4-diamino-2-nitrobenzene and its use for the preparation of $N^4$-($\beta$-hydroxyethyl)-5-methyl-1,4-diamino-2-nitrobenzene.

As is known, the alkylation or hydroxyalkylation of aromatic amines and diamines leads to mixtures (see, for example, Houben-Weyl, Methoden der Organischen Chemie (Methods of Organic Chemistry), Volume XI/1, 4th edition 1957, G. Thieme Verlag, Stuttgart, pages 26 and 311 et seq., DE-AS 1,569,807 and DE-OS 1,955,681). $N^4$-($\beta$-Hydroxyethyl)-5-chloro-1,4-diamino-2-nitrobenzene is thus also obtained in a yield of only 19.4% by conventional hydroxyethylation of 5-chloro-1,4-diamino-2-nitrobenzene in Preparation Example B of DE-AS 2,157,844. The reaction of aromatic amines with $\beta$-chloroethyl chloroformate or $\gamma$-chloropropyl chloroformate with subsequent treatment of the resulting chloroalkyl carbamates with a base has been described as an alternative for selective introduction of a $\beta$-hydroxyethyl or $\gamma$-hydroxypropyl radical (R. Adams and J. B. Segur, J. Am. Chem. Soc. 45, 785 (1923) and J. S. Pierce and R. Adams, J. Am. Chem. Soc. 45, 790 (1923)). Whereas reactions of amines with $\beta$-chloroethyl or $\gamma$-chloropropyl chloroformate are in general carried out in inert organic solvents, such as benzene, methyl isobutyl ketone, dioxane and the like, it is already known from the literature mentioned last that this reaction is to be carried out in water. Nevertheless, a) only aromatic monoamines are reacted, so that there is no selectivity problem, b) only aniline derivatives which are liquid or low-melting and likewise liquid under the reaction conditions and which react with the chloroformic acid esters mentioned in a homogeneous phase are employed, c) the chloroformic acid esters mentioned are added very rapidly to amine which has been initially introduced into water (they are poured in), so that they come into contact with the aqueous phase only briefly, and d) the amines are employed in a molar excess, so that the product and starting compound must be separated from one another by extraction by shaking.

The closest prior art which may be mentioned for the reaction of aromatic diamino compounds having two amino groups of different reactivity is the reaction, described in DE-OS 3,141,019, of 5-methyl-1,4-diamino-2-nitrobenzene with $\beta$-chloroethyl chloroformate. Dioxane has been used as the solvent here, to which about 22% of water was added. The chloroformic acid ester mentioned was in turn added rapidly (in the course of 10 minutes) to the diamine (see Comparison Example 2); no information is given regarding the selectivity of the reaction.

However, in the reaction of 1,4-diamino-2-nitrobenzenes of the general formula II with chloroformic acid esters of the formula Cl—COO—CH(A)—CH(B)—D—even if these are employed in less than the molar amount—in the presence of significant amounts of an organic solvent in the reaction medium, it is unavoidable that, in addition to the desired compounds of the general formula I a, certain amounts of compounds having the general formula III, wherein $R_1$, A, B and D have the abovementioned meanings, are also formed and are practically impossible to remove, or can be removed only with a considerable loss in yield, from the desired compounds (see Comparison Examples 1 and 2). As a consequence, dyestuffs of the general formula I b which are contaminated by certain amounts of dyestuffs of the general formula IV, wherein $R_1$, X, Y and Z have the abovementioned meanings, are always obtained in the second stage, and their convenience of handling and dyeing activity are thus impaired (see Comparison Example 3).

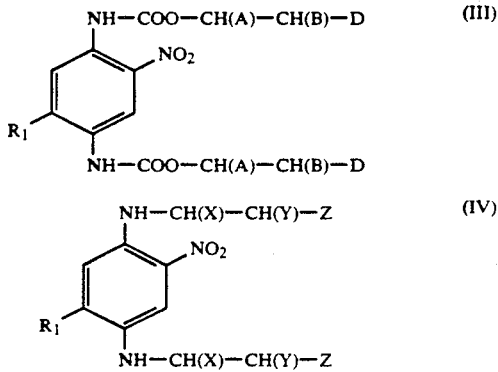

Surprisingly, it has now been found that these disadvantages can be avoided if the compounds of the general formula II are reacted in a predominantly aqueous reaction medium which contains—based on the water present—not more than 20 per cent by weight of an inert organic solvent (particularly suitable solvents are water-miscible solvents, such as dioxane, ethylene glycol dimethyl ether, diethylene glycol dimethyl ether, tetrahydrofuran, acetone, dimethylformamide, N-methylpyrrolidone and the like), and preferably in a purely aqueous medium, with chloroformic acid esters of the formula Cl—COO—CH(A)—CH(B)—D, wherein A, B and D have the abovementioned meaning. By the process according to the invention, it is possible to prepare particularly pure carbamates of the general formula I a which are practically free from bis-carbamates of the formula III, and in this way also to prepare, by treatment with a base, particularly pure dyestuffs of the general formula I b which are practically free from compounds of the formula IV and have significantly better properties in respect of their convenience of handling and their dyeing activity compared with the dyestuffs obtainable according to the prior art. This was not to be expected since the chloroformic acid esters mentioned are substances which are sensitive towards water. Thus, for example, β-chloroethyl chloroformate is hydrolyzed completely by hot water at 40° C. in the course of half an hour. With the proposed slow addition of the chloroformic acid esters, hydrolysis thereof even before the reaction, which takes place from a heterogeneous phase system, with the diamino compound of the general formula II, which is largely undissolved under the reaction conditions according to the invention, would have to be feared. The excellent selectivity of the process was also not to be predicted.

The compounds of the general formula Ib which can be prepared by the processes according to the invention and are new in some cases and known in some cases represent an important class of directly absorbing dyestuffs for hair colouring agents (see, for example, J. F. Corbett in "The Chemistry of Synthetic Dyes", Volume V, published by K. Venkataraman, Academic Press, New York 1971, pages 508–518).

Details of the process according to the invention, which also has advantages from the economic and from the ecological aspect, are described below.

To carry out the first stage, the equimolar amount or slightly less than the equimolar amount of the chloroformic acid ester of the formula Cl—COO—CH(A)—CH(B)—D is metered in the course of about 2-10 hours, and preferably in the course of about 3-6 hours, at about 40°-55° C. into a diamino compound of the general formula II, which has been initially introduced into a predominantly aqueous mixture, and preferably into pure water. The desired reaction takes place sufficiently rapidly in this temperature range, without formation of by-products and without hydrolysis of the chloroformic acid ester. This reaction is advantageously carried out in the presence of an acid-binding agent. Possible acid-binding agents are the customary inorganic or organic bases, such as, for example, alkali metal or alkaline earth metal hydroxides, bicarbonates or carbonates or tertiary amines, which can either be initially introduced at the same time or metered in simultaneously with the chloroformic acid ester. A particular advantage of the process lies in the use of calcium carbonate as the acid-binding agent, which, because it is sparingly soluble in water, can be initially introduced without in any way promoting hydrolysis of the chloroformic acid ester. When the reaction has ended, the carbamate of the general formula I a can then be filtered off directly.

To carry out the second stage, the carbamate is reacted with at least three times the molar amount of an alkali metal hydroxide solution. This reaction can be carried out in the customary manner in alcohol-water mixtures, preferably in the temperature range from about 40°-60° C., or in pure water, and in this case preferably at about 65°-85° C. When the reaction has ended, the pH can be neutralized from about 12-14 to 7-10 with the aid of an inorganic or organic acid, such as, for example, hydrochloric acid, sulphuric acid or acetic acid, and the dyestuff of the general formula I b—if appropriate after the solvent has been stripped off—can be filtered off directly, after the reaction mixture has cooled.

The process according to the invention is also particularly suitable for carrying out as a one-pot process. For this, the required amount of alkali metal hydroxide solution is added directly to the predominantly or purely aqueous reaction mixture containing the carbamate of the general formula I a—if appropriate after addition of a solvent, such as methanol, ethanol, propanol, isopropanol or ethylene glycol dimethyl ether—and further processing is carried out.

The following examples are intended to illustrate the process according to the invention without limiting it.

EXAMPLE 1

$N^4$-(β-Chloroethoxycarbonyl)-1,4-diamino-2-nitrobenzene 154 g (1 mol) of 1,4-diamino-2-nitrobenzene (99.4% pure) and 52 g of calcium carbonate are initially introduced into 1,000 ml of water, and 142 g of β-chloroethyl chloroformate (98.5% pure) are added at 45° C. in

| Analysis for $C_{10}H_{11}Cl_2N_3O_4$ (308.12) | | | |
|---|---|---|---|
| C | H | Cl | N |
| calculated: 38.98% | 3.60% | 23.01% | 13.64% |
| found: 39.2% | 3.6% | 23.4% | 13.7% |

EXAMPLE 8

$N^4$-($\gamma$-Chloropropoxycarbonyl)-5-methoxy-1,4-diamino-2-nitrobenzene 46 g (0.25 mol) of 5-methoxy-1,4-diamino-2-nitrobenzene are reacted with 39.3 g of $\gamma$-chloropropyl chloroformate under the conditions described in Example 6.

Yield: 72 g (96% of the theoretical value). Melting point: 141°-142° C.

After a single recrystallization from ethanol the melting point is 143° C.

| Analysis for $C_{11}H_{14}ClN_3O_5$ (303.70) | | | |
|---|---|---|---|
| C | H | Cl | N |
| calculated: 43.50% | 4.65% | 11.67% | 13.84% |
| found: 43.8% | 4.7% | 11.8% | 13.7% |

EXAMPLE 9

$N^4$-($\gamma$-Chloropropoxycarbonyl)-5-methyl-1,4-diamino-2-nitrobenzene 83.5 g (0.5 mol) of 5-methyl-1,4-diamino-2-nitrobenzene are reacted with 78.5 g of $\gamma$-chloropropyl chloroformate under the conditions described in Example 6.

Yield: 132 g (93% of the theoretical value). Melting point: 120°-122° C.

After a single recrystallization from toluene, the melting point is 125°-126° C.

| Analysis for $C_{11}H_{14}ClN_3O_4$ (287.70) | | | |
|---|---|---|---|
| C | H | Cl | N |
| calculated: 45.92% | 4.90% | 12.32% | 14.61% |
| found: 46.1% | 4.8% | 12.3% | 14.4% |

EXAMPLE 10

$N^4$-($\beta$-Hydroxyethyl)-1,4-diamino-2-nitrobenzene 260 g (1 mol) of the compound prepared according to Example 1 are initially introduced into 1100 ml of ethanol, and 350 g of 50% strength potassium hydroxide solution are added at 40°-50° C. in the course of about 2 hours. After a further 18 hours at 40°-50° C., 800 ml of water are added, the pH is brought to 8 with about 80 ml of glacial acetic acid, about 1100 ml of ethanol are distilled off at about 40° C. in vacuo and the reaction mixture is cooled to 10° C. The product is filtered off, washed with water and dried.

Yield: 186 g (96.4% pure, determined by spectrophotometry) (91% of the theoretical value). Melting point: 92° C.

The yield and purity of the product are considerably better than in Comparison Example 3. The thin layer chromatogram shows that it is practically free from $N^1$,$N^4$-bis-($\beta$-hydroxyethyl)-1,4-diamino-2-nitrobenzene. The convenience of handling and dyeing properties are significantly improved.

EXAMPLE 11

$N^4$-($\beta$-Hydroxyethyl)-1,4-diamino-2-nitrobenzene 175 g of 50% strength potassium hydroxide solution are added at 75°-80° C. in the course of about 1 hour to 130 g (0.5 mol) of the compound prepared according to Example 1 in 500 ml of water. After $\frac{1}{2}$-1 hour, the reaction mixture is cooled to 60° C., the pH is brought to 8 with about 40 ml of glacial acetic acid and the mixture is slowly cooled further to 10° C. The product is filtered off, washed with water and dried.

Yield: 92 g (94.3% pure) (88% of the theoretical value). Melting point: 88°-89° C.

The same advantages as those stated at the end of Example 10 apply.

EXAMPLE 12

$N^4$-($\beta$-Hydroxyethyl)-1,4-diamino-2-nitrobenzene 154 g (1 mol) of 1,4-diamino-2-nitrobenzene (99.4% pure) and 52 g of calcium carbonate are initially introduced into 100 ml of water, and 142 g of $\beta$-chloroethyl chloroformate (98.5% pure) are added at 45° C. in the course of about 4 hours. After a further 2 hours, the batch is diluted with 800 ml of ethanol, 342 g of 50% strength potassium hydroxide solution are added dropwise in the course of about 3 hours, the mixture is subsequently stirred at 45°-50° C. for 16 hours, the pH is then brought to 8 with about 80 ml of glacial acetic acid and about 800 ml of ethanol are distilled off at 40° C. in vacuo. After cooling to 10° C., the product is filtered off, washed with water and dried.

Yield: 202 g (87.2% pure) (91% of the theoretical value). Melting point: 89°-90° C.

The same advantages as those stated at the end of Example 10 apply.

EXAMPLE 13

$N^4$-($\beta$-Hydroxyethyl)-5-chloro-1,4-diamino-2-nitrobenzene 73.5 g (0.25 mol) of the compound prepared according to Example 2 are reacted with 87 g of 50% strength potassium hydroxide solution under the conditions described in Example 10.

Yield: 50.5 g (87% of the theoretical value). Melting point: 130° C.

EXAMPLE 14

$N^4$-($\beta$-Hydroxyethyl)-5-ethoxy-1,4-diamino-2-nitrobenzene 40 g (0.2 mol) of 5-ethoxy-1,4-diamino-2-nitrobenzene are reacted with 29 g of $\beta$-chloroethyl chloroformate under the conditions described in Example 12, the reaction mixture is further treated with 70 g of 50% strength potassium hydroxide solution as described in that example and is worked up in a corresponding manner and the desired compound of $R_F$ value 0.35 (silica gel, mobile phase toluene/2-butanol (7:3)) is isolated.

Yield: 23 g (47% of the theoretical value); Melting point: 157°-158° C. $\lambda_{max}$ (ethanol): 475 nm.

EXAMPLE 15

$N^4$-($\beta$-Hydroxyethyl)-5-methoxy-1,4-diamino-2-nitrobenzene 72.5 g (0.25 mol) of the compound prepared according to Example 4 are initially introduced into 300 ml of methanol, and 87 g of 50% strength potassium hydroxthe course of about 4 hours. After a further 2 hours, the product is filtered off, washed with water and dried.

Yield: 254 g (practically quantitative). Melting point: 149°–150° C.

It is remarkable that the yield and purity of the product are substantially better than in Comparison Example 1. The thin layer chromatogram shows that the product is free from $N^1,N^4$-bis-($\beta$-chloroethoxycarbonyl)-1,4-diamino-2-nitrobenzene.

After a single recrystallization from toluene, the melting point is 152° C.

| Analysis for $C_9H_{10}ClN_3O_4$ (259.65) | | | | |
|---|---|---|---|---|
| | C | H | Cl | N |
| calculated: | 41.63% | 3.88% | 13.65% | 16.18% |
| found: | 41.5% | 4.1% | 14.0% | 15.9% |

EXAMPLE 2

$N^4$-($\beta$-Chloroethoxycarbonyl)-5-chloro-1,4-diamino-2-nitrobenzene 94 g (0.5 mol) of 5-chloro-1,4-diamino-2-nitrobenzene are reacted with 71 g of $\beta$-chloroethyl chloroformate under the conditions described in Example 1.

Yield: 133 g (92% of the theoretical value). Melting point: 170°–171° C.

After a single recrystallization from toluene, the melting point is 178° C.

| Analysis for $C_9H_9Cl_2N_3O_4$ (294.10) | | | | |
|---|---|---|---|---|
| | C | H | Cl | N |
| calculated: | 36.76% | 3.08% | 24.11% | 14.29% |
| found: | 37.1% | 3.0% | 24.4% | 14.0% |

EXAMPLE 3

$N^4$-($\beta$-Chloroethoxycarbonyl)-5-fluoro-1,4-diamino-2-nitrobenzene 85.5 g (0.5 mol) of 5-fluoro-1,4-diamino-2-nitrobenzene (prepared in accordance with Example 1 of the patent application "New nitro-p-phenylenediamine derivatives, process for their preparation and colouring agents which contain these for keratinic fibres" filed at the same time, file ref.: German Patent Application P 3 917 114.0 (U.S. patent application Ser. No. 07/513,996)) are reacted with 71 g of $\beta$-chloroethyl chloroformate under the conditions described in Example 1.

Yield: 135 g (99% of the theoretical value). Melting point: 158°–159° C.

After a single recrystallization from toluene, the melting point is 160° C.

| Analysis for $C_9H_9ClFN_3O_4$ (277.64) | | | | | |
|---|---|---|---|---|---|
| | C | H | Cl | F | N |
| calculated: | 38.94% | 3.27% | 12.77% | 6.84% | 15.13% |
| found: | 39.1% | 3.2% | 12.9% | 6.8% | 15.0% |

EXAMPLE 4

$N^4$-($\beta$-Chloroethoxycarbonyl)-5-methoxy-1,4-diamino-2-nitrobenzene 91.5 g (0.5 mol) of 5-methoxy-1,4-diamino-2-nitrobenzene are reacted with 71 g of $\beta$-chloroethyl chloroformate under the conditions described in Example 1.

Yield: 132 g (91% of the theoretical value). Melting point: 139°–140° C.

After a single recrystallization from toluene, the melting point is 141°–142° C.

| Analysis for $C_{10}H_{12}ClN_3O_5$ (289.68) | | | | |
|---|---|---|---|---|
| | C | H | Cl | N |
| calculated: | 41.46% | 4.18% | 12.24% | 14.51% |
| found: | 41.4% | 4.0% | 12.3% | 14.5% |

EXAMPLE 5

$N^4$-($\beta$-Chloroethoxycarbonyl)-5-methyl-1,4-diamino-2-nitrobenzene 83.5 g (0.5 mol) of 5-methyl-1,4-diamino-2-nitrobenzene are reacted with 71 g of $\beta$-chloroethyl chloroformate under the conditions described in Example 1.

Yield: 130 g (97% of the theoretical value). Melting point: 188°–189° C.

The yield is considerably higher than that of Comparison Example 2.

After a single recrystallization from toluene/dioxane (1:1), the melting point is 193°–194° C.

EXAMPLE 6

$N^4$-($\gamma$-Chloropropoxycarbonyl)-1,4-diamino-2-nitrobenzene 77 g (0.5 mol) of 1,4-diamino-2-nitrobenzene (99.4% pure) and 26 g of calcium carbonate are initially introduced into 500 ml of water, and 78.5 g of $\gamma$-chloropropyl chloroformate (98.7% pure) are added at 45°–50° C. in the course of about 5 hours. After a further 2 hours, the product is filtered off, washed thoroughly with water and dried.

Yield: 135 g (practically quantitative). Melting point: 121° C.

After a single recrystallization from toluene, the melting point is 123° C.

| Analysis for $C_{10}H_{12}ClN_3O_4$ (273.68) | | | | |
|---|---|---|---|---|
| | C | H | Cl | N |
| calculated: | 43.89% | 4.42% | 12.95% | 15.35% |
| found: | 43.9% | 4.3% | 13.1% | 15.2% |

EXAMPLE 7

$N^4$-($\gamma$-Chloropropoxycarbonyl)-5-chloro-1,4-diamino-2-nitrobenzene 94 g (0.5 mol) of 5-chloro-1,4-diamino-2-nitrobenzene are reacted with 78.5 g of $\gamma$-chloropropyl chloroformate under the conditions described in Example 6.

Yield: 149 g (98% of the theoretical value). Melting point: 130°–131° C.

After a single recrystallization from toluene the melting point is 134° C.

ide solution are added at 45° C. in the course of 2 hours. After 18 hours at 45°-50° C., 300 ml of water are added, the pH is brought to 8 with about 20 ml of glacial acetic acid, about 300 ml of methanol are distilled off at 40° C. in vacuo, the batch is cooled to 10° C. and the desired compound of $R_F$ value 0.25 (silica gel, mobile phase toluene/2-butanol (7:3)) is isolated.

Yield: 30 g (53% of the theoretical value); Melting point: 165° C. $\lambda_{max}$ (ethanol): 475 nm.

EXAMPLE 16

$N^4$-(β-Hydroxyethyl)-5-methyl-1,4-diamino-2-nitrobenzene 68.5 g (0.25 mol) of the compound prepared according to Example 5 are reacted with 87 g of 50% strength potassium hydroxide solution under the conditions described in Example 10.

Yield: 47 g (89% of the theoretical value). Melting point: 139°-140° C.

EXAMPLE 17

$N^4$-(γ-Hydroxypropyl)-1,4-diamino-2-nitrobenzene 110 g (0.4 mol) of the compound prepared according to Example 6 are initially introduced into 450 ml of ethanol, and 140 g of 50% strength potassium hydroxide solution are added at 45° C. in the course of 2 hours. After a further 4 hours at 45° C. the mixture is left to stand at room temperature overnight, 450 ml of water are added, the pH is brought to 8 with about 25 ml of glacial acetic acid, about 400 ml of ethanol are distilled off at 40° C. in vacuo and the reaction mixture is cooled to 10° C. The product is filtered off, washed with water, recrystallized from ethanol and dried.

Yield: 65 g (77% of the theoretical value); Melting point: 104° C. $\lambda_{max}$ (ethanol): 494 nm.

EXAMPLE 18

$N^4$-(γ-Hydroxypropyl)-5-chloro-1,4-diamino-2-nitrobenzene 124 g (0.4 mol) of the compound prepared according to Example 7 are reacted with 140 g of 50% strength potassium hydroxide solution under the conditions described in Example 17.

Yield: 81 g (82% of the theoretical value); Melting point: 138° C. $\lambda_{max}$ (ethanol): 484 nm.

EXAMPLE 19

$N^4$-(γ-Hydroxypropyl)-5-ethoxy-1,4-diamino-2-nitrobenzene 40 g (0.2 mol) of 5-ethoxy-1,4-diamino-2-nitrobenzene are reacted with 31.5 g of γ-chloropropyl chloroformate under the conditions described in Example 12, the reaction mixture is treated further with 70 g of 50% strength potassium hydroxide solution as described in that example and is worked up in a corresponding manner and the product is recrystallized from ethanol.

Yield: 38 g (74% of the theoretical value); Melting point: 124° C. $\lambda_{max}$ (ethanol): 480 nm.

EXAMPLE 20

$N^4$-(γ-Hydroxypropyl)-5-methoxy-1,4-diamino-2-nitrobenzene 61 g (0.2 mol) of the compound obtained according to Example 8 are reacted with 70 g of 50% strength potassium hydroxide solution under the conditions described in Example 15, the mixture is worked up in a corresponding manner and the product of $R_F$ value 0.24 (silica gel, mobile phase toluene/2-butanol (7:3)) is isolated.

Yield: 37 g (76% of the theoretical value); Melting point: 156° C. $\lambda_{max}$ (ethanol): 480 nm.

EXAMPLE 21

$N^4$-(γ-Hydroxypropyl)-5-methyl-1,4-diamino-2-nitrobenzene 116 g (0.4 mol) of the compound prepared according to Example 9 are reacted with 140 g of 50% strength potassium hydroxide solution under the conditions described in Example 17.

Yield: 73 g (81% of the theoretical value). Melting point: 148°-149° C.

COMPARISON EXAMPLE 1

$N^4$-(β-Chloroethoxycarbonyl)-1,4-diamino-2-nitrobenzene 77 g (0.5 mol) of 1,4-diamino-2-nitrobenzene and 26 g of calcium carbonate are initially introduced into 230 ml of dioxane, and 70 g of β-chloroethyl chloroformate are added at 70°-80° C. in the course of about 1 hour. After 1-2 hours, the inorganic salts are filtered off hot and the product is allowed to crystallize out in the filtrate. The crystals are filtered off with suction, washed with a little dioxane and dried.

Yield: 105 g (81% of the theoretical value; further amounts can be obtained by concentrating or diluting the mother liquor). Melting point: 125°-130° C.

After three recrystallizations from toluene, the melting point is 141°-142° C. In the thin layer chromatogram, $N^1$, $N^4$-bis-(β-chloroethoxycarbonyl)-1,4-diamino-2-nitrobenzene is still clearly detectable as a by-product.

COMPARISON EXAMPLE 2

$N^4$-(β-Chloroethoxycarbonyl)-5-methyl-1,4-diamino-2-nitrobenzene (prepared in accordance with DE-OS 3,141,019, step 1 of Preparation Example 1)

83.5 g (0.5 mol) of 5-methyl-1,4-diamino-2-nitrobenzene and 41.5 g of potassium carbonate are initially introduced into 417 ml of dioxane and 121 ml of water, and 71.7 g of β-chloroethyl chloroformate are added at 90° C. in the course of 10 minutes. The reaction mixture is subsequently stirred at 90° C. for a further 10 minutes and then cooled to 15° C. The product is filtered off, washed with a little dioxane and then with water and alcohol and dried.

Yield: 109 g (81% of the theoretical value). Melting point: 191°-192° C.

$N^1$,$N^4$-bis-(β-chloroethoxycarbonyl)-5-methyl-1,4-diamino-2-nitrobenzene is clearly detectable as a by-product in the thin layer chromatogram of the mother liquor. After a single recrystallization from toluene/dioxane (1:1), the melting point is 193°-194° C.

COMPARISON EXAMPLE 3

$N^4$-(β-Hydroxyethyl)-1,4-diamino-2-nitrobenzene 65 g (0.25 mol) of the compound prepared in Comparison Example 1 are reacted with 87 g of 50% strength potassium hydroxide solution under the conditions described in Example 10.

Yield: 47 g (86.8% pure) (82.8% of the theoretical value). Melting point: 74°-82° C.

$N^1,N^4$-Bis-($\beta$-hydroxyethyl)-1,4-diamino-2-nitrobenzene is clearly detectable as a by-product in the thin layer chromatogram.

The contaminated dyestuff of this comparison example shows significantly poorer properties than the pure dyestuff of Examples 10, 11 or 12 in respect of its convenience in handling and its dyeing properties.

I claim:

1. Process for the selective preparation of $N^4$-substituted 1,4-diamino-2-nitrobenzenes of the general formula I

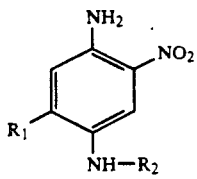
(I)

in which $R_1$ denotes hydrogen, halogen, ($C_1$-$C_4$) alkyl or ($C_1$-$C_4$) alkoxy, it being possible for the carbon atoms to be arranged in straight-chain or branched form, and $R_2$ represents a radical —COO—CH(A)—CH(B)—D with the meanings A=H, B=H, D=Cl, A=H, B=CH$_3$, D=Cl, A=H, B=H, D=CH$_2$Cl or A=CH$_3$, B=H and D=Cl (compounds of the general formula Ia) or a radical —CH(X)—CH(Y)—Z with the meanings X=H, Y=H, Z=OH, X=CH$_3$, Y=H, Z=OH, X=H, Y=H, Z=CH$_2$OH or X=H, Y=CH$_3$ and Z=OH (compounds of the general formula Ib)

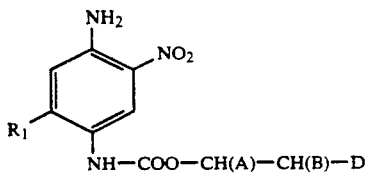
(Ia)

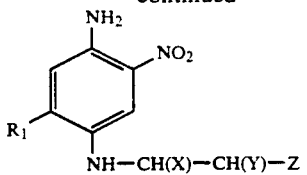
(Ib)

characterized in that 1,4-diamino-2-nitrobenzenes of the general formula II

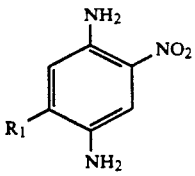
(II)

wherein $R_1$ has the abovementioned meaning, are reacted in a first stage with an approximately equimolar amount of a chloroalkyl chloroformate of the general formula Cl—COO—CH(A)—CH(B)—D, wherein A, B and D have the above-mentioned meanings, in a predominantly aqueous medium which contains—based on the water present—not more than 20 per cent by weight of an organic solvent, to give carbamates of the general formula Ia and if appropriate these carbamates are converted into compounds of the general formula Ib in a second stage by means of treatment with a base.

2. Process according to claim 1, characterized in that the reaction of the first stage is carried out in a purely aqueous medium.

3. Process according to claim 1 characterized in that the first stage is carried out at a temperature of about 40°-55° C.

4. Process according to one of claim 1 characterized in that the first stage is carried out in the presence of calcium carbonate as an acid-binding agent.

5. Process according to one of claim 1 characterized in that the two stages of the process are carried out as a one-pot reaction.

6. Process according to one of claim 1 for the preparation of $N^4$-($\beta$-hydroxyethyl)-1,4-diamino-2-nitrobenzene.

* * * * *